United States Patent [19]

Hofmeister et al.

[11] Patent Number: 4,642,368
[45] Date of Patent: Feb. 10, 1987

[54] NOVEL ESTERS, THEIR PREPARATION, AND THEIR USE FOR CONTROLLING PESTS

[75] Inventors: Peter Hofmeister, Ludwigshafen; Rainer, Buerstinghaus, Weinheim; Heinrich Adolphi, Limburgerhof, all of Fed. Rep. of Germany

[73] Assignee: BASF Aktiengesellschaft, Fed. Rep. of Germany

[21] Appl. No.: 713,644

[22] Filed: Mar. 19, 1985

[30] Foreign Application Priority Data

Mar. 22, 1984 [DE] Fed. Rep. of Germany ....... 3410543

[51] Int. Cl.⁴ .............................................. C07C 69/76
[52] U.S. Cl. ...................................... 560/65; 514/544; 549/430; 560/51; 560/113; 560/64
[58] Field of Search ............................ 560/64, 65, 113; 574/544; 549/430

[56] References Cited

U.S. PATENT DOCUMENTS

| 3,288,834 | 11/1966 | Sterling et al. | 560/64 |
| 3,828,031 | 8/1974 | Karrer | 260/240 H |
| 3,957,833 | 5/1976 | Chodnekar et al. | 549/560 |
| 3,996,379 | 12/1976 | Mihailouski | 560/113 |
| 3,996,380 | 12/1976 | Henrick | 560/64 |
| 4,084,062 | 4/1978 | Mihailouski | 560/113 |
| 4,259,350 | 3/1981 | Morisawa et al. | 560/1 |

FOREIGN PATENT DOCUMENTS

| 0095117 | 5/1983 | European Pat. Off. | 59/68 |
| 8072540 | 4/1983 | Japan | 560/113 |

Primary Examiner—Paul J. Killos
Attorney, Agent, or Firm—Keil & Weinkauf

[57] ABSTRACT

Propargyl esters of the formula I

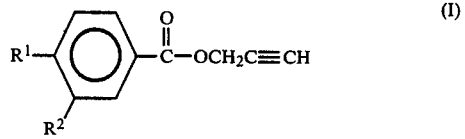

where $R^1$ is $OC_nH_{2n+1}$ (n=1 or 2), $OCF_3$, $OCF_2CHF_2$ or F and $R^2$ is H, or $R^1$ and $R^2$ together form $-O(CH_2)_mO-$ (m=1 or 2), a process for their preparation, and their use for controlling pests.

4 Claims, No Drawings

NOVEL ESTERS, THEIR PREPARATION, AND THEIR USE FOR CONTROLLING PESTS

The present invention relates to special novel propargyl esters, a process for their preparation, pesticides which contain these esters as active ingredients, and a method of controlling pests with these active ingredients.

It has been disclosed that alkyl esters of alkynoic acids or alkynyl esters are useful for controlling mites (U.S. Pat. Nos. 4,024,278 and 3,996,380). However, the effect is restricted to arachnids.

We have found that esters of the formula I

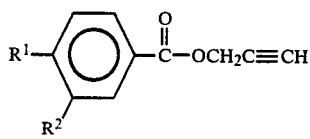

where $R^1$ is $OC_nH_{2n+1}$ (n=1 or 2), $OCF_3$, $OCF_2CHF_2$ or F and $R^2$ is H, or $R^1$ and $R^2$ together form $-O(CH_2)_mO-$ (m=1 or 2), possess very good insecticidal, acaricidal and, in particular, ovicidal activity and are superior to known active ingredients having a similar structure or the same direction of action.

The esters of the formula I can be obtained by reacting the corresponding acids II with propargyl alcohol (cf. Houben-Weyl, Methoden der organ. Chemie, volume VIII, page 516 et seq., Georg-Thieme-Verlag, Stuttgart 1952).

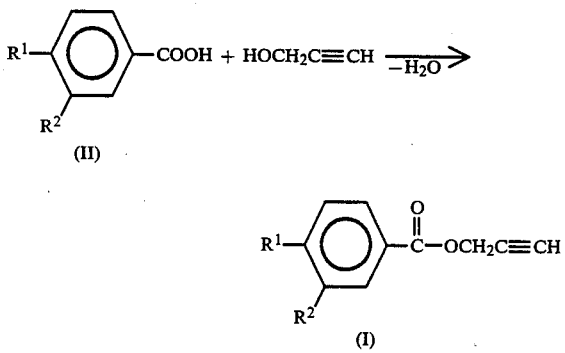

The reaction can be accelerated in a conventional manner by the addition of a catalyst, such as sulfuric acid, a hydrogen halide, a sulfonic acid or an acidic ion exchanger, and the equilibrium of the esterification can be shifted in the desired direction by removing the water or the ester I from the reaction mixture, for example by azeotropic distillation or by binding the water to sulfuric acid or a hydrohalic acid.

It is also possible to react the corresponding acid halides III with propargyl alcohol in the presence of an acid acceptor (cf. Houben-Weyl, Methoden der organ. Chemie, volume VIII, page 541 et seq., Georg-Thieme-Verlag, Stuttgart 1952).

Suitable acid acceptors are the conventional basic agents, in particular aliphatic, aromatic and heterocyclic amines, eg. triethylamine, dimethylamine, piperidine, dimethylaniline, dimethylbenzylamine and pyridine.

The reaction can be carried out in a solvent or diluent, suitable solvents or diluents being the stated acid acceptors themselves or, for example, the following solvents or diluents or mixtures of these: aliphatic and aromatic hydrocarbons and chlorohydrocarbons, such as petroleum ether, benzene, toluene, xylene, gasoline, dichloromethane, chloroform, tetrachloromethane, 1,2-dichloroethane or chlorobenzene, ethers, such as diethyl ether, di-n-butyl ether, methyl tert.-butyl ether, tetrahydrofuran or dioxane, ketones, eg. acetone, methyl ethyl ketone or methyl isopropyl ketone, and nitriles, such as acetonitrile or propionitrile.

The starting materials are usually employed in a stoichiometric ratio, but an excess of one or other of the starting materials may be quite advantageous in specific cases.

The reaction usually takes place at an adequate rate at above 0° C. Since it generally proceeds with evolution of heat, it may be advantageous to provide a means of cooling.

Furthermore, the esters according to the invention can be prepared by virtually any conventional method of ester synthesis, for example by reacting an appropriate anhydride with propargyl alcohol, by reacting an appropriate salt with a propargyl halide, or by transesterification (cf. Houben-Heyl loc.cit., pages 508-628).

The substituted benzoic acids of the formula II which are required as starting materials are known, and some or all of them are available commercially; some of the acid chlorides prepared from them in certain cases were obtained as described in Houben-Weyl, loc.cit., pages 463-476.

All of the novel compounds of the formula I can be prepared by appropriately modifying the Example below:

EXAMPLE 1

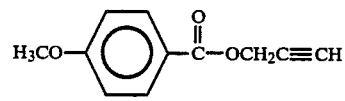

6.2 g (0.11 mole) of propargyl alcohol in 50 ml of pyridine are initially taken, and 17.1 g (0.10 mole) of anisyl chloride are added dropwise, while cooling in an ice bath. The mixture is then stirred for 24 hours at room temperature, after which it is poured into ice water, and the precipitated product is filtered off under suction, washed with 2nHCl and water, and dried. 18.1 g (95.3% yield) of a colorless crystalline solid of melting point 47°-48° C. are obtained.

$C_{11}H_{10}O_3$ (190)—calculated: C, 69.5; H, 5.3. found: C, 69.6; H, 5.5.

60 MHz-$^1$H-NMR spectrum in $CDCl_3$ (—values in ppm). 2.55 (t, 1H); 3.87 (s, 3H); 4.93 (d, 1H); 6.94 (d, 2H); 8.05 (d, 2H).

TABLE 1

| Example | $R^1$ | $R^2$ | $^1$H—NMR data (60 MHz, $CDCl_3$, values in ppm) |
|---|---|---|---|
| 2 | $OCF_3$ | H | 2.57 (t, 1H), 4.95 (d, 2H), 7.28 (d, 2H), 8.17 (d, 2H) |
| 3 | $OCH_2CH_3$ | H | 1.43 (t, 3H), 2.56 (t, 1H), 4.09 (q, 2H), 4.89 (d, 2H), 6.88 (d, 2H), 8.01 (d, 2H) |
| 4 | $OCF_2CHF_2$ | H | 2.57 (t, 1H), 4.92 (d, 2H), 5.93 (tt, 1H), 7.27 (d, 2H), 8.10 (d, 2H) |
| 5 | F | H | 2.55 (t, 1H), 4.91 (d, 2H), 6.98-7.42 (m, 2H), 7.98-8.35 |

TABLE 1-continued

| Example | R$^1$ | R$^2$ | $^1$H—NMR data (60 MHz, CDCl$_3$, values in ppm) |
| --- | --- | --- | --- |
| 6 | | —OCH$_2$O— | (m, 2H) 2.53 (t, 1H), 4.90 (d, 1H), 6.08 (d, 2H), 6.87 (d, 1H), 7.52 (s, 1H), 7.72 (d, 2H) |

The propargyl esters of the formula I can be used for effective control of pests from the class consisting of the insects and arachnids. They can be used as pesticides for crop protection, in the hygiene sector, for the protection of stored materials and in the veterinary sector, and act preferably on the eggs of the pests.

The active ingredients listed above and other novel active ingredients are used in the manner conventionally employed for insecticides. Information concerning formulation, application techniques, mode of action and suitable mixing components for achieving synergistic and other advantageous effects can be found in, for example, U.S. Pat. No. 4,320,122, which is herein incorporated by reference.

The concentration of active ingredients in the ready-to-use formulations can be varied within wide ranges. In general, they are from 0.00001 to 10%, preferably from 0.001 to 0.1%.

Under open air conditions, the application rate for the active ingredient is from 0.02 to 10, preferably from 0.1 to 2.0, kg/ha.

USE EXAMPLE 1

The active ingredient described in Example 1 has a good specific action against insect eggs; the following results were obtained in the immersion test:

| Dysdercus | at 0.01% | 100% mortality |
| --- | --- | --- |
| Prodenia | at 0.01% | about 80% mortality |
| Agrotis | 0.004% | about 80% mortality |
| Heliothis | 0.004% | about 80% mortality |
| Ephestia | 0.1% | 100% mortality |
| Colorado beetle | 0.02% | 100% mortality |

(Percentages are based on active ingredient in aqueous solution).

A substantial effect was also observed in the spray strip test at an application rate of 400 l/ha, the following results being obtained:

| For Plutella eggs | at 0.1% | about 90% mortality |
| --- | --- | --- |
| For Prodenia eggs | at 0.1% | about 80% mortality |
| For Heliothis eggs | at 0.04% | about 90% mortality |
| For Epilachna eggs | at 0.1% | 100% mortality |

USE EXAMPLES 2–7

For the use examples below, the following were employed as comparative agents:

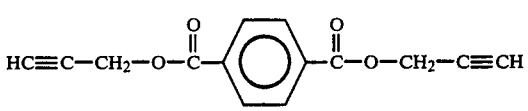

I

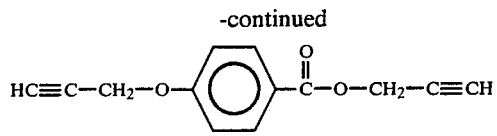

II both of these are described in U.S. Pat. No. 3,996,380 as being effective in the context of the invention.

Action on eggs of the cotton stainer (*Dysdercus intermedius*)

About 200 freshly laid eggs of the cotton stainer are attached to adhesive strips, and these are dipped into the aqueous active ingredient formulation. The strips are then stored at 25° C. and 70% relative humidity until the untreated control hatches.

Result:

| Example | % | % Mortality |
| --- | --- | --- |
| 1 | 0.01 | 100 |
| 2 | 0.1 | 100 |
| 3 | 0.04 | 100 |
| 4 | 0.02 | 100 |
| 5 | 0.002 | 100 |
| 6 | 0.01 | 100 |
| Comparative agent I | 0.1 | 40 |

Action on eggs of *Ostrinia nubilalis*

The female moths lay their eggs in closed groups on parchment paper. Two days after the eggs have been laid, paper strips which have been cut out and which carry about 200–300 eggs are dipped for about 5 seconds into the aqueous active ingredient formulation and then placed on moist wadding in a Petri dish (diameter 10 cm).

Evaluation is carried out after hatching of the control, which begins after 5 to 6 days.

Result:

| Example | % | % Mortality |
| --- | --- | --- |
| 1 | 0.01 | 100 |
| 6 | 0.01 | 100 |
| Comparative agent II | 0.01 | about 90 |

Action on eggs of *Prodenia litura*

The female moths lay their eggs in closed groups on parchment paper. Two days after the eggs have been laid, paper strips which have been cut out and which carry about 200–300 eggs are dipped for about 5 seconds into the aqueous active ingredient formulation and then placed on moist wadding in a Petri dish (diameter 10 cm).

Evaluation is carried out after hatching of the control, which begins after 5 to 6 days.

Result:

| Example | % | % Mortality |
| --- | --- | --- |
| 1 | 0.01 | about 80 |
| 4 | 0.02 | about 80 |
| 5 | 0.01 | about 90 |
| Comparative agent II | 0.01 | about 20 |

Action on eggs of *Agrotis ypsilon*

The female moths lay their eggs in closed grops on parchment paper. Two days after the eggs have been laid, paper strips which have been cut out and which carry about 200–300 eggs are dipped for about 5 seconds into the aqueous active ingredient formulation and then placed on moist wadding in a Petri dish (diameter 10 cm).

Evaluation is carried out after hatching of the control, which begins after 5 to 6 days.

Result:

| Example | % | % Mortality |
|---------|-------|-------------|
| 1 | 0.004 | 80 |
| 6 | 0.004 | 100 |

Active on eggs of *Heliothis virescens*

Two-day old eggs of Heliothis virescens are dipped into the aqueous active ingredient formulation for about 5 seconds and then placed on moist wadding in a Petri dish.

Evaluation is carried out after the untreated control has hatched.

Result:

| Example | % | % Mortality |
|---------|------|-------------|
| 1 | 0.01 | about 90 |
| 6 | 0.01 | about 90 |
| Comparative agent II | 0.01 | about 40 |

Action on eggs of the Colorado beetle (*Leptinotarsa decemlineata*)

Two day old eggs of the Colorado beetle, together with the leaf on which they have been laid, are dipped into the aqueous active ingredient formulation for about 5 seconds and then placed on moist wadding in a Petri dish.

Evaluation is carried out after the untreated control has hatched.

Result:

| Example | % | % Mortality |
|---------|------|-------------|
| 1 | 0.02 | 100 |
| 1 | 0.01 | about 90 |
| Comparative agent II | 0.01 | about 50 |

We claim:

1. An ester of the formula I

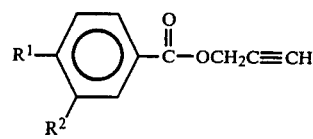

where $R^1$ is $OC_nH_{2n+1}$ (n=1 or 2), $OCF_3$, $OCF_2CHF_2$ or F and $R^2$ is H, or $R^1$ and $R^2$ together form $-O(CH_2)_mO-$ (m=1 or 2).

2. A pesticide containing a solid or liquid carrier and an effective amount of one or more esters of the formula I as defined in claim 1.

3. A method of controlling pests, wherein an effective amount of an ester of the formula I as claimed in claim 1 is allowed to act on pests or their habitat.

4. An ester of the formula I as defined in claim 1, wherein $R^1$ is F and $R^2$ is H.

* * * * *